United States Patent
Shin et al.

(10) Patent No.: US 10,040,809 B2
(45) Date of Patent: Aug. 7, 2018

(54) METHOD FOR PREPARING TRIS(TRIALKYLSILYL)PHOSPHINE

(71) Applicant: SK CHEMICALS CO., LTD., Gyeonggi-do (KR)

(72) Inventors: Yong-Jun Shin, Seoul (KR); Suk Woon Jun, Gyeonggi-do (KR); Jeong Ho Park, Gyeonggi-do (KR)

(73) Assignee: SK CHEMICALS CO., LTD., Gyeonggi-do (KR)

( * ) Notice: Subject to any disclaimer, the term of this patent is extended or adjusted under 35 U.S.C. 154(b) by 0 days.

(21) Appl. No.: 15/501,283

(22) PCT Filed: Nov. 6, 2015

(86) PCT No.: PCT/KR2015/011872
§ 371 (c)(1),
(2) Date: Feb. 2, 2017

(87) PCT Pub. No.: WO2016/080683
PCT Pub. Date: May 26, 2016

(65) Prior Publication Data
US 2017/0226138 A1 Aug. 10, 2017

(30) Foreign Application Priority Data

Nov. 18, 2014 (KR) .......................... 10-2014-0161080

(51) Int. Cl.
*C07F 9/02* (2006.01)
*C07F 9/06* (2006.01)

(52) U.S. Cl.
CPC ....................................... *C07F 9/06* (2013.01)

(58) Field of Classification Search
None
See application file for complete search history.

(56) References Cited

U.S. PATENT DOCUMENTS 2,907,785 A   10/1959   George et al. ............. 260/448.2

FOREIGN PATENT DOCUMENTS

DE    0274626        12/1989   ............... C07F 9/50
DE    274626 A1 *    12/1989   ............... C07F 7/08
                                              9/50

OTHER PUBLICATIONS

Uhlig et al Z. anorg. allg. Chem. 576 (1989) 281-283.*
Uhlig et al., Z. anorg allg. Chem., 576, 1989, 281-283. (Year: 1989).*
Third Party Documents—Concise_Description_of_Relevance; Jan. 19, 2018. (Year: 2018).*
ISR dated Feb. 4, 2016 in PCT/KR2015/011872 published in WO 2016/080683.
Kaesz, H. D., et al., (1959). "Preparation and characterization of vinyldichlorophosphine, vinyldimethylphosphine, and ethyldimethylphosphine". *J. Org. Chem.* 24:635-637.
Uhlig, W. et al., (1985). "Eine neue method zur darstellung von organosilylphosphinen". *Z. Anorg. Allgem. Chem.* 576:281-283.
Uhlig, W., et al., A New Method for the Preparation of Organosilylphosphines, Z. anorg. Allg. Chem. 576 , pp. 281-283, 1989.
Fuchs, Philip L, ed., Tris(Trimethylsilyl)Phosphine, Handbook of Reagents for Organic Synthesis: Reagents for Silicon-Mediated Organic Synthesis, pp. 422-427, attached pages labeled, pp. 1-5, 2011.
Ionkin, A., et al., A stable enol in small ring systems: clear differentiation between penta- and tri-valency of phosphorus atoms, Chem. Commun., pp. 5432-5434, 2008.
Smallwood, Ian, ed., Handbook of Organic Solvent Properties, pp. 135-165, 1996.

* cited by examiner

*Primary Examiner* — Clinton A Brooks
*Assistant Examiner* — Kofi Adzamli
(74) *Attorney, Agent, or Firm* — Harness, Dickey & Pierce, P.L.C.

(57) ABSTRACT

The present invention relates to a method for preparing a tris(trialkylsilyl)phosphine in high yield and high purity with safety and no risk of fire or explosion.

11 Claims, No Drawings

METHOD FOR PREPARING TRIS(TRIALKYLSILYL)PHOSPHINE

CROSS-REFERENCE TO RELATED APPLICATIONS

This application is a national phase application of PCT Application No. PCT/KR2015/011872, filed on Nov. 6, 2015, which claims the benefit and priority of Korean Patent Application No. 10-2014-0161080, filed Nov. 18, 2014. The entire disclosures of the applications identified in this paragraph are incorporated herein by reference.

FIELD

The present invention relates to a method for preparing a tris(trialkylsilyl)phosphine in high yield and high purity with safety and no risk of fire.

BACKGROUND

Tris(trialkylsilyl)phosphines have been considered for use in the manufacture of semiconductors and display-related products. Tris(trimethylsilyl)phosphine (hereinafter, also referred to as "TMSP"), which is most widely known among tris(trialkylsilyl)phosphines, is increasingly used as a precursor for providing phosphine.

Known methods for producing TMSP generally employ solvents for uniformity of the reaction and high yield and purity of the product. Typical methods for producing TMSP are as follows: (1) introducing white phosphorus and a Na/K alloy to diglyme solvent through a dropping funnel, and adding chlorotrimethylsilane thereto (G. Beeker, W. Holderch, *Chem. Ber.* 108, 2484, 1975); (2) introducing red phosphorus and a Na/K alloy to 1,2-dimethylethane (DME) solvent through a dropping funnel, and adding chlorotrimethylsilane thereto (*Synthetic Methods of Organometallic and Inorganic Chemistry*, Herrmann/Brauer, Vol. 3, 1996, Georg Thieme Verlag Stuttgart New York); (3) reacting phosphorus trichloride and chlorotrimethylsilane with magnesium in hexamethylphosphoric acid triamide (HMPT) or tetrahydrofurane (THF) solvent (H. Schumann, L. Rosch, *Chem. Ber.* 107, 854, 1974); (4) reacting sodium with white phosphorus in THF solvent to produce sodium phosphide, and adding to sodium phosphide chlorotrimethylsilane in DME solvent to react them (F. R. Askham, G. G. Stanley, E. C. Marques, *J. Am. Chem. Soc.* 107, 7423, 1985); and (5) reacting phosphine with trimethylsilane triflate (TMSOTf) and triethylamine in dimethyl ether solvent (W. Uhlig, A. Tzschach, *Z. Anorg, Allgem. Chem.* 576, 281, 1988).

The above conventional methods, however, use an excess of metals such as sodium and potassium, which readily react with oxygen in the air to cause spontaneous ignition. The methods also employ organic solvents such as THF, ethers, DME, diglyme, etc., which are in essence inflammable or generate explosive by-products such as peroxides during the process. Accordingly, they may involve disadvantages that entrainment of oxygen into the process would not only decrease the purity of products but also increase the risk of fire and explosion. Especially, the method in which phosphine is reacted with TMSOTf and triethylamine in dimethyl ether solvent generates solid salts during the reaction, which should be removed by follow-up processes such as filtration, distillation, etc., to increase the purity of the product. Filtration is the most dangerous process in the manufacture of combustible materials, since filtration under positive pressures has a risk of fire due to release of combustible materials into the air, and filtration under negative pressures may give rise to explosion or fire in case of entrainment of external air.

Furthermore, a tris(trialkylsilyl)phosphine by itself readily reacts with oxygen in the air to cause strongly spontaneous ignition. Accordingly, it should be handled in an atmosphere of an inert gas such as nitrogen and helium with oxygen blocked. Entrainment of oxygen during the manufacture, storage, or transportation thereof may not only deteriorate the quality of products, but also cause spontaneous ignition and fire. Furthermore, since organic solvents may aggravate the possibilities of fire and explosion, special care is necessary in the process design and operation, as well as handling of the solvents. For the above reasons, these conventional methods for preparing tris(trialkylsilyl)phosphines have disadvantages of high investment and operation costs.

DISCLOSURE OF INVENTION

Technical Problem

An object of the present invention is to provide a method for preparing a tris(trialkylsilyl)phosphine in high yield and high purity, the method having improved safety without the risk of fire, explosion, etc., and being economically feasible with reduced process steps.

Solution to Problem

The present invention provides a method for preparing a tris(triC$_{1-5}$alkylsilyl)phosphine, which comprises the steps of:

(1) preparing a mixture of a halogenated hydrocarbon, a triC$_{1-5}$alkylsilyl triflate, and a tertiary amine;

(2) adding phosphine to the mixture prepared in step (1); and (3) adding a triC$_{1-5}$alkylsilyl triflate to the mixture prepared in step (2).

Advantageous Effects

According to the present invention, the method has improved safety by using a solvent with a reduced risk of ignition and is economically feasible with reduced process steps, as well as it can prepare a tris(trialkylsilyl)phosphine in high yield and high purity.

BEST MODE

The method for preparing a tris(triC$_{1-5}$alkylsilyl)phosphine according to the present invention comprises the steps of (1) preparing a mixture of a halogenated hydrocarbon, a triC$_{1-5}$alkylsilyl triflate, and a tertiary amine; (2) adding phosphine to the mixture prepared in step (1); and (3) adding a triC$_{1-5}$alkylsilyl triflate to the mixture prepared in step (2).

The method for preparing a tris(triC$_{1-5}$alkylsilyl)phosphine according to the present invention relates to a synthesis of organic silyl phosphine compounds from the starting materials of phosphorus and silicone compounds, which is represented by the reaction scheme below:

[Scheme 1]

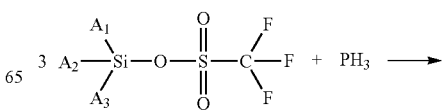

-continued

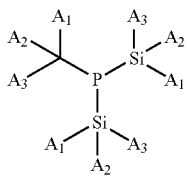

In Scheme 1, $A_1$, $A_2$ and $A_3$, which may be the same or different, are each independently $C_{1-5}$ alkyl.

The $C_{1-5}$ alkyl can be, for example, methyl, ethyl, propyl, isopropyl, butyl, 2-butyl, or t-butyl.

Step (1)

In step (1) of the present invention, a mixture of a halogenated hydrocarbon, a $triC_{1-5}$alkylsilyl triflate, and a tertiary amine may be prepared.

Although the present method may be carried out without a solvent, it would decrease the yield and purity of the product; therefore, it is preferred to use a solvent in the present method. Preferably, the solvent is an organic solvent, which is not reactive in the reaction conditions and is nonflammable with no risk of fire. Accordingly, halogenated hydrocarbons are used as the solvent of the present invention.

Although halogenated hydrocarbons are typically known as polar and nonflammable materials, they are not used in a highly reactive reaction that employs a polar solvent or a material having a risk of fire. Further, since some halogenated hydrocarbons are decomposed to be acidic and also used as oxidizing agents for oxidation reactions, they are much less used in reactions using highly reactive materials. Furthermore, since halogenated hydrocarbons are known to react with white phosphorus to form a phosphorus-carbon bond, they are not considered to be preferable as solvents in many conventional methods of producing TMSP in high yield and high purity. The present inventors, however, have focused on the nonflammability of halogenated hydrocarbons and intensively studied to find that halogenated hydrocarbons are stabile in the process on a large scale of reaction and are capable of producing TMSP in high yield and high purity.

The halogenated hydrocarbons are represented by Formula 1:

$$C_aH_bX_c \quad \text{[Formula 1]}$$

wherein

X is a halogen atom, a is an integer of $1 \leq a \leq 5$, b is an integer of $2a-c+2$, and c is an integer of $c \geq 2a$.

In Formula 1, the halogen atom may be selected from the group consisting of fluorine, chlorine, and bromine. Preferably, the halogen atom may be chlorine.

The halogen atoms of the halogenated hydrocarbon used in the present invention may be the same or different. Considering the economic feasibility, however, it is preferred to use the same halogens.

The halogenated hydrocarbon may be at least one selected from the group consisting of difluoromethane, trifluoromethane, tetrafluoromethane, tetrafluoroethane, pentafluoroethane, hexafluoroethane, dichloromethane, chloroform, carbon tetrachloride, tetrachloroethane, pentachloroethane, hexachloroethane, hexachloropropane, heptachloropropane, octachloropropane, dibromomethane, tribromomethane, tetrabromomethane, tetrabromoethane, pentabromoethane, and hexabromoethane, but is not limited thereto.

The halogenated hydrocarbon may be substituted by chlorine, which is inexpensive and is not reactive to other materials. Accordingly, the halogenated hydrocarbon may be at least one selected from the group consisting of dichloromethane, chloroform, carbon tetrachloride, tetrachloroethane, pentachloroethane, hexachloroethane, hexachloropropane, heptachloropropane, and octachloropropane. Preferably, the halogenated hydrocarbon may be dichloromethane or tetrachloroethane.

The halogenated hydrocarbon may have a boiling point of 10° C. or higher, for example, 10 to 200° C. at atmospheric pressure.

The halogenated hydrocarbon may be in an amount of 1 to 200 parts by weight, 1 to 100 parts by weight, 2 to 50 parts by weight, or 5 to 20 parts by weight per 1 part by weight of the $triC_{1-5}$alkylsilyltriflate, depending on the convenience of handling, stability of reaction, yield of reaction, and purity of product. If the amount of the halogenated hydrocarbon is less than 1 part by weight per 1 part by weight of the $triC_{1-5}$ alkylsilyl triflate, the reaction could not be well controlled and the yield of reaction and the purity of product could be impaired. On the other hand, an amount exceeding 200 parts by weight per 1 part by weight of the $triC_{1-5}$ alkylsilyl triflate may lower the economic feasibility, make it difficult to handle the reactants, and decrease the yield of reaction.

In addition, a $triC_{1-5}$alkylsilyl triflate is used in step (1) of the present invention.

The term "$triC_{1-5}$alkyl," as used in the $triC_{1-5}$alkylsilyl triflate, may refer to three $C_{1-5}$ alkyl groups, each of which is independently selected from the group consisting of methyl, ethyl, propyl, isopropyl, butyl, isobutyl, t-butyl, pentyl, 2-pentyl, isopentyl, neopentyl, and 3-methylbutyl.

The $triC_{1-5}$alkylsilyl triflate may be selected from the group consisting of, for example, trimethylsilyl triflate, triethylsilyl triflate, tripropylsilyl triflate, tributylsilyl triflate, dimethylethylsilyl triflate, methyldiethylsilyl triflate, dimethylpropylsilyl triflate, methyldipropylsilyl triflate, dimethylbutylsilyl triflate, methyldibutylsilyl triflate, and diethylpropylsilyl triflate, but is not limited thereto. Specifically, triethylsilyl triflate, trimethylsilyl triflate, or dimethylethylsilyl triflate is preferably used.

Furthermore, in step (1) of the present invention, a base such as a tertiary amine may be used.

The tertiary amine may have at least one substituent selected from the group consisting of methyl, ethyl, propyl, isopropyl, butyl, isobutyl, t-butyl, and phenyl.

The tertiary amine may be selected from the group consisting of, for example, trimethylamine, triethylamine, tripropylamine, tributylamine, triphenylamine, dimethylethylamine, methyldiethylamine, dimethylpropylamine, methyldipropylamine, methylethylpropylamine, diethylpropylamine, ethyldipropylamine, and ethyldiisopropylamine. Specifically, triethylamine is preferably used.

The tertiary amine may be used in an amount of 0.5 to 2 equivalents by mole, based on the $triC_{1-5}$alkylsilyl triflate.

Step (2)

In step (2) of the present invention, phosphine may be added to the mixture prepared in step (1).

The phosphine may be added after the mixture prepared in step (1) is cooled to 10° C. or lower, preferably 0 to 10° C., in an ice bath or with a cooling apparatus.

The phosphine may be added in an amount of 0.2 to 3 equivalents by mole, based on the $triC_{1-5}$alkylsilyl triflate.

The phosphine may be introduced by bubbling it into the mixture through a tube such as a cannula. Alternatively, it may be introduced directly in gas phase or as a solution dissolved in a solvent.

Step (3)

In step (3) of the present invention, a triC$_{1-5}$alkylsilyl triflate may be further added to the mixture obtained in step (2).

The triC$_{1-5}$alkylsilyl triflate may be added in an amount of 50 parts by weight or less, preferably 5 to 40 parts by weight, based on 100 parts by weight of the triC$_{1-5}$alkylsilyl triflate used in step (1). Subsequently, the reactor is heated to room temperature, and the reaction is further performed for 10 minutes to 3 hours until the completion of reaction.

According to the present invention, the further addition of a triC$_{1-5}$alkylsilyl triflate in step (3) facilitates the preparation of a tris(triC$_{1-5}$alkylsilyl)phosphine in higher yield.

The reaction mixture obtained in step (3) may be distilled under a reduced pressure to remove solvents, unreacted reactants, and by-products, to thereby produce the aimed tris(triC$_{1-5}$alkylsilyl)phosphine. According to the present invention, if necessary, further processes such as filtration, absorption, and distillation under reduced pressures may be performed to enhance the purity of the obtained product.

In the conventional methods for preparing a tris(triC$_{1-5}$alkylsilyl)phosphine with an organic solvent such as dimethyl ether, salts insoluble in the solvent are formed during the reaction, which requires follow-up processes such as filtration, distillation, etc., to increase the purity of product. Furthermore, since the objective compound tris(triC$_{1-5}$alkylsilyl)phosphine by itself reacts with oxygen in the air to form impurities and is spontaneously ignitable, the processes of filtration and transportation for the filtration should be carried out in an atmosphere of an inert gas such as nitrogen or argon. Accordingly, the conventional methods require high level techniques and expensive facilities.

In contrast, the method of the present invention has improved safety without a risk of fire and explosion by using halogenated hydrocarbons with low inflammability. Furthermore, no insoluble salts are formed during the reaction in the present invention, which allows the preparation of a tris(trialkylsilyl)phosphine in high yield and high purity even without follow-up processes such as filtration, distillation, etc.

MODE FOR THE INVENTION

Hereinafter, the present invention is described in detail with reference to the following examples. However, these examples are merely presented to exemplify the present invention, and the scope of the present invention is not limited thereto.

The Examples and Comparative Examples below were performed under an inert atmosphere, and analyses were conducted by NMR analysis in the presence of anhydrous benzene-D$_6$ solvent at 600 MHz. All solvents used in the reaction and analysis were dehydrated through molecular sieve before use.

Example 1: Preparation of Tris(Trimethylsilyl)Phosphine 90 mL of trimethylsilyl triflate and 104 mL of triethylamine were added to 1 L of dichloromethane at room temperature, and the mixture was stirred to be mixed (step 1).

The mixture was cooled to 10° C. or lower in an ice bath. When the temperature of the mixture reached about 8° C., phosphine gas was introduced thereto through a cannula at a rate of 10 mL/minute. Supply of phosphine was stopped after a total of 9 g of phosphine was introduced (step 2).

After 30 mL of trimethylsilyl triflate were added to the reaction mixture obtained above, the mixture was heated to room temperature and then allowed to further react for 1 hour (step 3).

The reaction mixture in liquid phase thus obtained was, without filtration, distilled under reduced pressures to obtain 50.5 g (yield: 92%) of the objective compound tris(trimethylsilyl)phosphine.

Purity (%): 99%

$^{31}$P-NMR (Benzene-d$_6$, 600 MHz) δ −251.9 (s)

Example 2: Preparation of Tris(Dimethylethylsilyl)Phosphine

The procedure of Example 1 above was repeated except that dimethylethylsilyl triflate was used instead of trimethylsilyl triflate in Steps 1 and 3 to obtain 51.9 g (yield: 81%) of tris(dimethylethylsilyl)phosphine.

Purity (%): 98%

$^{31}$P-NMR (Benzene-d$_6$, 600 MHz) δ −250.8 (s)

Example 3: Preparation of Tris(Triethylsilyl)Phosphine

The procedure of Example 1 above was repeated except that triethylsilyl triflate was used instead of trimethylsilyl triflate in Steps 1 and 3 to obtain 72.7 g (yield: 88%) of tris(triethylsilyl)phosphine.

Purity (%): 98%

$^{31}$P-NMR (Benzene-d$_6$, 600 MHz) δ −249.1 (s)

Example 4: Preparation of Tris(Trimethylsilyl)Phosphine

The procedure of Example 1 above was repeated except that tetrachloroethane (Sigma-Aldrich Co. LLC.) was used instead of dichloromethane in step 1 to obtain 49.4 g (yield: 90%) of tris(trimethylsilyl)phosphine.

Purity (%): 99.2%

$^{31}$P-NMR (Benzene-d$_6$, 600 MHz) δ −251.9 (s)

Comparative Example 1: Preparation of Tris(Trimethylsilyl)Phosphine 90 mL of trimethylsilyl triflate and 104 mL of triethylamine were added to 1 L of dimethyl ether at room temperature, and the mixture was stirred to be mixed.

The mixture was cooled to 10° C. or lower in an ice bath. When the temperature of the mixture reached about 8° C., phosphine gas was introduced thereto through a cannula at a rate of 10 mL/minute. Supply of phosphine was stopped after a total of 9 g of phosphine was introduced.

After 30 mL of trimethylsilyl triflate were added to the reaction mixture obtained above, the mixture was heated to room temperature and then allowed to further react for 1 hour.

After the stirring was stopped, the reaction mixture obtained in slurry was transported by pressurized nitrogen and filtered through celite under a nitrogen atmosphere. The filtrate obtained in liquid phase was distilled under reduced pressures to obtain 37.3 g (yield: 68%) of the objective compound tris(trimethylsilyl)phosphine.

Purity (%): 96%
$^{31}$P-NMR (Benzene-d$_6$, 600 MHz) δ −251.9 (s)

Comparative Example 2: Preparation of Tris(Trimethylsilyl)Phosphine

The procedure of Example 1 above was repeated except that 40 mL of dichloromethane were added in step 1 to obtain 22.5 g (yield: 41%) of tris(trimethylsilyl)phosphine.
Purity (%): 92.9%
$^{31}$P-NMR (Benzene-d$_6$, 600 MHz) δ −251.9 (s)

Comparative Example 3: Preparation of Tris(Trimethylsilyl)Phosphine

The procedure of Example 1 above was repeated except that step 3 was not performed to obtain 39.5 g (yield: 72%) of tris(trimethylsilyl)phosphine.
Purity (%): 94.1%
$^{31}$P-NMR (Benzene-d$_6$, 600 MHz) δ −251.9 (s)

What is claimed is:

1. A method for preparing a tris(triC$_{1-5}$alkylsilyl)phosphine, comprising the steps of:
   (1) preparing a mixture of a halogenated hydrocarbon, a triC$_{1-5}$alkylsilyl triflate, and a tertiary amine;
   (2) adding phosphine to the mixture prepared in step (1); and
   (3) adding a triC$_{1-5}$alkylsilyl triflate to the mixture prepared in step (2),
   wherein the halogenated hydrocarbon is represented by Formula 1:

$C_aH_bX_c$     [Formula 1], wherein
   X is a halogen atom,
   a is an integer of 1≤a≤5,
   b is an integer of 2a−c+2, and
   c is an integer of c≥2a,
   wherein the tertiary amine has at least one substituent selected from the group consisting of methyl, ethyl, propyl, isopropyl, butyl, isobutyl, t-butyl, and phenyl, and
   wherein the method does not comprise a filtration step.

2. The method of claim 1, wherein the halogenated hydrocarbon has a boiling point of 10 to 200° C. at atmospheric pressure.

3. The method of claim 1, wherein the halogenated hydrocarbon is at least one selected from the group consisting of difluoromethane, trifluoromethane, tetrafluoromethane, tetrafluoroethane, pentafluoroethane, hexafluoroethane, dichloromethane, chloroform, carbon tetrachloride, tetrachloroethane, pentachloroethane, hexachloroethane, hexachloropropane, heptachloropropane, octachloropropane, dibromomethane, tribromomethane, tetrabromomethane, tetrabromoethane, pentabromoethane, and hexabromoethane.

4. The method of claim 3, wherein the halogenated hydrocarbon is at least one selected from the group consisting of dichloromethane, chloroform, carbon tetrachloride, tetrachloroethane, pentachloroethane, hexachloroethane, hexachloropropane, heptachloropropane, and octachloropropane.

5. The method of claim 1, wherein the triC$_{1-5}$alkyl in the triC$_{1-5}$alkylsilyl triflate is three C$_{1-5}$ alkyl groups, each of which is independently selected from the group consisting of methyl, ethyl, propyl, isopropyl, butyl, isobutyl, t-butyl, pentyl, 2-pentyl, isopentyl, neopentyl, and 3-methylbutyl.

6. The method of claim 5, wherein the triC$_{1-5}$alkylsilyl triflate is selected from the group consisting of trimethylsilyl triflate, triethylsilyl triflate, tripropylsilyl triflate, tributylsilyl triflate, dimethylethylsilyl triflate, methyldiethylsilyl triflate, dimethylpropylsilyl triflate, methyldipropylsilyl triflate, dimethylbutylsilyl triflate, methyldibutylsilyl triflate, and diethylpropylsilyl triflate.

7. The method of claim 1, wherein the tertiary amine is selected from the group consisting of trimethylamine, triethylamine, tripropylamine, tributylamine, triphenylamine, dimethylethylamine, methyldiethylamine, dim ethylpropylamine, methyldipropylamine, methylethylpropylamine, diethylpropylamine, ethyldipropylamine, and ethyldiisopropylamine.

8. The method of claim 1, wherein, in step (1), the halogenated hydrocarbon is in an amount of 1 to 200 parts by weight per 1 part by weight of the triC$_{1-5}$alkylsilyl triflate.

9. The method of claim 1, wherein, in step (2), the phosphine is added after the mixture prepared in step (1) is cooled to 0 to 10° C.

10. The method of claim 1, wherein, in step (2), the phosphine is added in an amount of 0.2 to 3 equivalents by mole, based on the triC$_{1-5}$alkylsilyltriflate.

11. The method of claim 1, wherein, in step (3), the triC$_{1-5}$alkylsilyltriflate is added in an amount of 5 to 40 parts by weight, based on 100 parts by weight of the triC$_{1-5}$alkylsilyltriflate used in step (1).

* * * * *